United States Patent [19]

Illy

[11] 4,142,029
[45] Feb. 27, 1979

[54] BIS-TETRAZOLES AS CHEMICAL BLOWING AGENTS FOR FOAMING THERMOPLASTIC RESINS

[75] Inventor: Hugo Illy, Reinach, Switzerland

[73] Assignee: Ciba-Geigy Corporation, Ardsley, N.Y.

[21] Appl. No.: 814,827

[22] Filed: Jul. 12, 1977

[30] Foreign Application Priority Data

Jul. 16, 1976 [CH] Switzerland .......................... 9138/76

[51] Int. Cl.² ............................................... C08J 9/10
[52] U.S. Cl. ................................. 521/95; 260/308 D; 521/142; 521/146; 521/147; 521/149; 521/180; 521/182; 521/189
[58] Field of Search ............... 260/2.5 E, 2.5 N, 2.5 P, 260/308 D

[56] References Cited

U.S. PATENT DOCUMENTS

| | | | |
|---|---|---|---|
| 3,442,829 | 5/1969 | Moore et al. | 260/2.5 HA |
| 3,615,616 | 10/1971 | Williams et al. | 96/109 |
| 3,873,477 | 3/1975 | Beck et al. | 260/2.5 HA |

*Primary Examiner*—Morton Foelak
*Attorney, Agent, or Firm*—Luther A. R. Hall

[57] ABSTRACT

Bis-tetrazoles wherein the two tetrazole rings are bridged by a direct bond or a divalent organic residue in 5,5'-position or in 1,1'-position have been found to be suitable as blowing agents for thermoplastic resins. They decompose at temperatures of about 230 to 300° C. and therefore can be used for the expansion of resins which are processed at such temperatures, for instance polypropylene, polycarbonates, polyphenyleneoxides or polyamides. Preferred are bis-tetrazoles bridges by aliphatic or araliphatic residues. The expansion can be carried out in an extruder or an injection moulding device.

6 Claims, No Drawings

BIS-TETRAZOLES AS CHEMICAL BLOWING AGENTS FOR FOAMING THERMOPLASTIC RESINS

The invention relates to a process for foaming thermoplastic materials (thermoplasts) by adding chemical blowing agents which decompose when heated and give off gas.

The production of foamed moulded shapes from thermoplastics by addition of chemical blowing agents in the moulding process, for example during injection moulding or extrusion, has been known for a long time. The decomposition of the blowing agent occurs in the plasticised thermoplastic material, and the decomposition temperature should be between the softening temperature of the thermoplastic material and the maximum processing temperature. The decomposition temperature of the blowing agent should preferably be about 20° C. below the maximum processing temperature in order to obtain a homogeneous cellular structure and maximum utilisation of the blowing agent.

The decomposition of the blowing agent has therefore to occur within a relatively narrow temperature range. The gas formed on decomposition should be odorless and inert. The blowing agent should break down completely into gaseous decomposition products, or alternatively the non-gaseous decomposition products should be soluble in the plastics material, and must not lead to discoloration or to changes in the physical or chemical properties of the plastics material.

The blowing agents hitherto known do not in most cases satisfy all these requirements, and are therefore suitable mainly only for specific fields of application. Thus, for example, organic hydrazides and semicarbazides split off ammonia, as a result of which polyesters or polycarbonates can be ammonolytically broken down. The known azodicarbonamide forms solid decomposition residues which are insoluble in the customary thermoplasts. Its use moreover is associated with a considerable smell contamination during foaming. 5-Phenyltetrazole has already been suggested as a blowing agent, especially for the foaming of thermoplasts having relatively high processing temperatures. This blowing agent leads neither to a smell nuisance not to a formation of residues; it produces however a gas yield lower than that of azodicarbonamide, and tends to cause discoloration if it is not completely decomposed.

It was the object of the invention to find chemical blowing agents for foaming thermoplastic materials, which blowing agents do not have the disadvantages described and which at the same time produce a gas yield higher than that of 5-phenyltetrazole.

It has been found that compounds suitable as blowing agents for the foaming of thermoplastic materials are the bis-tetrazoles of the formula I, II or III

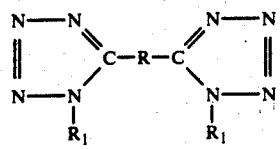

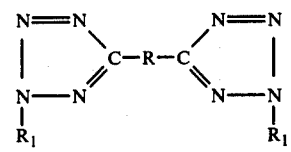

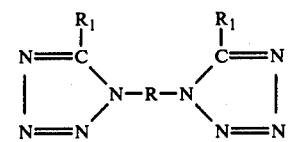

wherein $R_1$ represents hydrogen, $C_1$-$C_4$-alkyl, $C_5$-$C_6$-cycloalkyl, phenyl, naphthyl, or phenyl substituted by $C_1$-$C_4$-alkyl, $C_1$-$C_4$-alkoxy or halogen, and R represents a direct bond, or a straight-chain or branched-chain alkylene group which has 1–10 C atoms and which can be substituted by phenyl, benzyl, halogen, nitro, hydroxyl, $C_1$-$C_4$-alkoxy, formyl, $C_2$-$C_5$-alkanoyl, benzoyl or cyclohexylcarbonyl, or R represents an alkylene group which has 2–8 C atoms and which is interrupted by —O—, —S—, —$SO_2$— or —NY—, wherein Y represents hydrogen, $C_1$-$C_4$-alkyl, phenyl, naphthyl, cyclohexyl, benzyl, or a group of the formula $R_2$CO— or $R_2SO_2$—, and $R_2$ represents $C_1$-$C_4$-alkyl, phenyl, or phenyl substituted by $C_1$-$C_4$-alkyl, halogen or $C_1$-$C_4$-alkoxy, or R represents an alkenylene or alkynylene group each having 2–8 C atoms, or a radical of the formula —Ar—$(CH_2)_m$—, —$(CH_2)_m$—Ar—$(CH_2)_m$—, —$(CH_2)_m$—O—Ar—O—$(CH_2)_m$—, —NH—$(CH_2)_m$—NH—Ar—NH—$(CH_2)_m$—, —$(CH_2)_m$—Ar—X—Ar—$(CH_2)_m$—, —$(CH_2)_m$—O—Ar—X—Ar—O—$(CH_2)_m$— or —$(CH_2)_m$—NH—Ar—X—Ar—NH—$(CH_2)_m$—, wherein m represents 1 or 2, and Ar represents a phenylene or naphthylene group, which can be substituted by halogen, $NO_2$, alkyl or alkoxy each having 1–4 C atoms, and X represents a direct bond, —O—, —S—, —$SO_2$—, —$CH_2$—, —$C(CH_3)_2$— or —CO—, or R represents a bivalent heterocyclic radical of the formula —$(CH_2)_n$-Het$(CH_2)_n$-, wherein n represents 0, 1 or 2, and Het represents a 5- or 6-membered, non-condensed or condensed hetero ring having 1 to 3 N, O or S atoms, or a radical of the formula

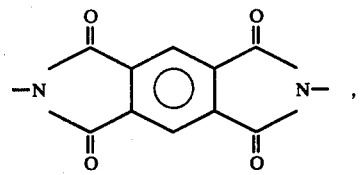

or R represents in the formula III a group of the formula —Ar— or —Ar—X—Ar— or, if $R_1$ is not hydrogen, represents also in the formula I or II a group of the formula —Ar— or —Ar—X—Ar—.

If $R_1$ represents $C_1$-$C_4$-alkyl, it can be methyl, ethyl, propyl, butyl or isobutyl. If $R_1$ represents $C_5$-$C_6$-cycloalkyl, it can be cyclopentyl or cyclohexyl. As substituted phenyl, $R_1$ can be for example tolyl, xylyl, 4-isopropoxyphenyl or 3-chlorophenyl.

Where R represents a straight-chain alkylene group, it can be a methylene or polymethylene group. In the case of a branched-chain alkylene group, R can be, for example, 1,2-propylene, 2,2-dimethyl-1,3-propylene, diethyl-methylene or 1,2-decylene.

If R represents a substituted alkylene group, this can be, for example, 2-phenyl-1,3-propylene, 1,2-diphenylethylene, benzylmethylene, 1,2-dichloroethylene, 4-nitro-1,5-pentylene, 2-hydroxy-1,3-propylene, 2,3-dihydroxy-1,4-butylene, acetyl-methylene, 3-formyl-1,5-pentylene, 3-phenyl-3-benzoyl-1,5-pentylene, 3-acetyl-3-methyl-1,5-pentylene, 3-benzoyl-1,5-pentylene or 3,3-dibenzoyl-1,5-pentylene.

If R is an interrupted alkylene group, it can be for example one of the following groups: —$CH_2OCH_2$—, —$CH_2CH_2OCH_2CH_2$—, —$CH_2SCH_2$—, —$CH_2CH_2SCH_2CH_2$—, —$CH_2OCH_2CH_2OCH_2$—, —$CH_2SO_2(CH_2)_4SO_2CH_2$—, —$CH_2N(CH_3)CH_2$—, —$CH_2CH_2N(C_3H_7)CH_2CH_2$—, —$CH_2CH_2N(CH_2C_6H_5)CH_2CH_2$—, —$CH_2CH_2N(C_6H_5)CH_2CH_2$—, —$CH_2CH_2N(COC_2H_5)CH_2CH_2$—, —$CH_2CH_2N(COC_6H_5)CH_2CH_2$—, —$CH_2CH_2N(SO_2C_6H_4$—p—$CH_3)CH_2CH_2$— or —$CH_2CH_2NCH_2CH_2NCH_2CH_2$—.

As an alkenylene or alkynylene group, R can be for example vinylene, but-2-enylene-1,4, but-2-inylene-1,4 or prop-1-enylene-2,3. Het as a bivalent 5- or 6-membered heterocyclic radical can be, for example, furan-2,5-diyl, 2-oxoimidazole-1,3-diyl, thiophene-2,5-diyl, pyridine-3,4-diyl, pyrazine-2,3-diyl, piperazine-1,4-diyl, 2,5-dioxopiperazine-1,4-diyl, 5,5-dimethylhydantoin-1,3-diyl, benzimidazolone-1,3-diyl or 2,3-dihydroquinoxaline-1,4-diyl.

If Y or $R_2$ represents $C_1$-$C_4$-alkyl, this can be methyl, ethyl, propyl, isopropyl, butyl, isobutyl or tert.-butyl.

As a substituted phenyl group, $R_2$ can be for example tolyl, xylyl, butylphenyl, chlorophenyl, dichlorophenyl or methoxyphenyl.

Preference is given to the use of bis-tetrazoles of formula I wherein $R_1$ represents $C_1$-$C_4$-alkyl, phenyl, or phenyl substituted by $C_1$-$C_4$-alkyl or chlorine, preferably represents however hydrogen, and R represents a direct bond, an alkylene group which has 1-10 C atoms and which can be substituted by phenyl, benzyl, hydroxyl, formyl, $C_2$-$C_5$-alkanoyl or benzoyl, or a $C_2$-$C_8$-alkylene group interrupted by —O—, —S—, —$SO_2$— or —NY, wherein Y represents $C_1$-$C_4$-alkyl, phenyl, benzyl, $R_2$CO— or $R_2SO_2$—, and $R_2$ represents $C_1$-$C_4$-alkyl, phenyl or tolyl, or R represents $C_2$-$C_8$-alkenylene, $C_2$-$C_8$-alkynylene, or a radical of the formula —$(CH_2)_m$—Ar—$(CH_2)_m$— or —$(CH_2)_m$—Ar—X—Ar—$(CH_2)_m$—, wherein m represents 1 or 2, Ar represents phenylene or naphthylene which can be substituted by $C_1$-$C_4$-alkyl, $C_1$-$C_4$-alkoxy, halogen or $NO_2$, and X represents a direct bond, —O—, —S—, —$SO_2$—, —$CH_2$— or —CO—, or, if $R_1$ is not hydrogen, R represents $C_6$-$C_{12}$-arylene or —Ar—X—Ar—.

Also preferred is the use of bis-tetrazoles of the formula I wherein $R_1$ represents hydrogen, R represents a direct bond or a straight-chain or branched-chain alkylene group which has 1-10 C atoms and which can be substituted by 1 or 2 phenyl or benzyl groups, an alkylene group which has 2-8 C atoms and which is interrupted by —O—, —S—, —$SO_2$— or —NY—, wherein Y represents alkyl having 1-4 C atoms, phenyl or benzyl, an alkenylene or alkynylene group each having 2-8 C atoms, or a radical of the formula —$(CH_2)_m$—Ar—$(CH_2)_m$— or —$(CH_2)_m$—Ar—X—Ar—$(CH_2)_m$—, wherein m represents 1 or 2, and Ar represents a phenylene or naphthylene group which can be substituted by halogen, $NO_2$, alkyl or alkoxy each having 1-4 C atoms, and X represents a direct bond, —O—, —S—, —$SO_2$—, —$CH_2$— or —CO—.

The compounds of the formula I wherein $R_1$ represents hydrogen have a tautomeric relationship to the corresponding compounds of the formula II, that is to say, the hydrogen can be both in the 1-position and in the 2-position of the tetrazole ring. These compounds can be represented therefore also by the following formula IV

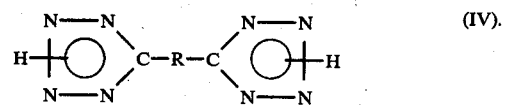

Particularly preferred is the use of bis-tetrazoles of the formula I wherein $R_1$ represents hydrogen, $C_1$-$C_4$-alkyl or phenyl, and R represents a direct bond, an alkylene group which has 1-8 C atoms and which can be substituted by 1 or 2 phenyl or benzyl groups, an alkylene group which has 2-6 C atoms and which is interrupted by —O—, —S—, —$SO_2$— or —NY—, wherein Y represents phenyl, benzoyl, benzenesulphonyl or toluenesulphonyl, or a radical of the formula —$CH_2$—Ar—$CH_2$— or —$CH_2$—Ar—X—Ar—$CH_2$—, wherein Ar represents phenylene, and X represents a direct bond or —O—.

The compounds of the formula I or II wherein $R_1$ represents hydrogen (= compounds of the formula IV) can be produced by methods known per se, for example by the method described in J. Amer. Chem. Soc. 80, 3908 (1958), which method comprises reacting a corresponding dinitrile NC—R—CN with hydrazoic acid. The performing of such reactions is described in greater detail in the Examples given further on in the text.

Examples of applicable dinitriles on NC—R—CN are: dicyanogen, malondinitrile, succinic acid dinitrile, glutaric acid dinitrile, adipic acid dinitrile, 2-methylglutaric acid dinitrile, mono- and dibenzylmalodintrile, diethylmalodintrile, 2,3-diphenylsuccinic acid dinitrile, malic acid nitrile, tartaric acid nitrile, β-hydroxyglutaric acid dintrile, 4-nitropimelic acid dinitrile, 4-benzoyl-4-phenylpimelic acid dinitrile, 4-acetyl-4-methylpimelic acid dinitrile, 4-formylpimelic acid dinitrile, 4-acetyl-4-isopropylpimelic acid dinitrile, 4-benzoylpimelic acid dinitrile, di-(cyanomethyl)-ether, 3,3′-ethylenedioxy-dipropionitrile, 3,3′-tetramethylenedioxy-dipropionitrile, 3,3′-(oxy-bis-ethyleneoxy)-dipropionitrile, 3-cyanomethoxy-prionitrile, 3,3′-oxydipropionitrile, 3,3′-thio-dipropionitrile, 3,3′-sulpho-dipropionitrile, 3,3′-iminodipropionitrile, 3,3′-methylimino-dipropionitrile, 3,3′-phenylimino-dipropionitrile, 3,3′-(p-tolylimino)-dipropionitrile, 3,3′-(2-naphthylimino)-dipropionitrile, N,N-bis-(2-cyanoethyl)-benzenesulphonamide, N,N-bis-(2-cyanoethyl)-benzamide, N,N-bis-(2-cyanoethyl)-acetamide, N,N′-bis-(2-cyanoethyl)-ethylenediamine, o-, p- and m-di-(cyanomethyl)-benzene, 4,4′-di-(cyanomethyl)-diphenyl, resorcinol-bis-(cyanoethyl ether), 2,2-diphenylolpropane-bis-(2-cyanoethyl ether), N,N′-bis-(2-cyanoethyl)-p-phenylenediamine, N,N′-bis-(2-cyanoethyl)-1,4-naphthylenediamine, 4,4′-bis-(cyanomethyl)-diphenyl oxide, 4,4′-bis-(cyanomethyl)-diphenylmethane, N,N′-bis-(2-cyanoethyl)-4,4′-diaminodiphenylsulphone, 2-oxoimidazolone-1,3-dipropionitrile, piperazine-1,4-diacetonitrile, 1,2-dicyanopyrazine, 2,5-dicyanothiophene, 1,3-bis-(cyanomethyl)-5,5-dimethylhydantoin, N,N'-bis-(2-cyanoethyl)-benzimidazolone or 2,3-dihydroquinoxaline-1,4-dipropionitrile.

Compounds of the formula I wherein $R_1$ does not represent hydrogen can be produced from N-substituted dicarboxylic acid amides of the formula $R_1$—NH—CO—R—CO—NH—$R_1$ by reaction with $PCl_5$ or $SOCl_2$, and reaction of the resulting imide chlorides with alkali azide, in the manner described in Chem. Ber. 42, (1909), 2336 and 74, (1941), 264.

Examples of such substituted dicarboxylic acid amides are: terephthalic acid-di-(methylamide), terephthalic acid dianilide, terephthalic acid-di-(cyclohexylamide), phthalic acid dianilide, isophthalic acid-di-(methylamide), oxalic acid-di-(methylamide), oxalic acid-di-(ethylamide), oxalic acid-di-(tert.-butylamide), succinic acid dianilide, malonic acid-di-(methylamide), adipic acid-di-(methylamide) or sebacic acid-di-(methylamide).

Compounds of the formula II wherein $R_1$ represents an aryl radical can be produced from bis-guanylhydrazones of the formula

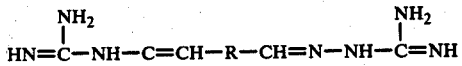

by coupling with diazonium salts, and subsequent reaction with nitrous acid, in the manner described in Chem. Ber. 30, (1897), 449 and 31, (1898), 475. Examples of applicable starting materials are the bis-guanylhydrazones of glyoxal, isophthal aldehyde, terephthal aldehyde or 4,4'-diformyldiphenyl ether.

Compounds of the formulae I and II wherein $R_1$ represents alkyl or cycloalkyl can be produced from the compounds in which $R_1$ represents H by N-substitution, for example by reaction with alkyl halides or alkyl tosylates in the presence of bases. There are formed mixtures of the alkylated compounds of the formulae I and II, which can be separated by known methods.

The 1,1-bound bis-tetrazoles of the formula III can be produced from N,N'-diacyl-diamines of the formula $R_1$—CONH—R—NHCO—$R_1$ by reaction with $PCl_5$ or $SOCl_2$, and reaction of the resulting bis-imide chlorides with alkali azide. Examples of suitable diacyldiamines are: N,N'-diacetyl-p-phenylenediamine, N,N'-dibenzoyl-m-phenylenediamine, N,N'-diacetyl-ethylenediamine, N,N'-dibenzoyl-propylene-1,2-diamine or N,N'-diformyl-naphthylene-1,4-diamine.

Some of the bis-tetrazoles usable according to the invention are known compounds which have been suggested, for example, for photographic application (see, e.g., GB Patent specification No. 1,207,855); however, their application as blowing agents for the foaming of plastics has not been known hitherto.

The greater part of the bis-tetrazoles defined in the foregoing are new compounds. These are on the one hand those compounds of the formula I, II or III wherein $R_1$ represents $C_1$-$C_4$-alkyl, $C_5$-$C_6$-cycloalkyl, phenyl, naphthyl, or phenyl substituted by $C_1$-$C_4$-alkyl, $C_1$-$C_4$-alkoxy or halogen, and in the case of the formula III $R_1$ also represents hydrogen, and R represents a direct bond, or a straight-chain or branched-chain alkylene group which has 1-10 C atoms and which can be substituted by phenyl, benzyl, halogen, nitro, hydroxyl, $C_1$-$C_4$-alkoxy, formyl, $C_2$-$C_5$-alkanoyl, benzoyl or cyclohexylcarbonyl, or R represents an alkylene group which has 2-8 C atoms and which is interrupted by —O—, —S—, —$SO_2$— or —NY—, wherein Y represents hydrogen, $C_1$-$C_4$-alkyl, phenyl, naphthyl, cyclohexyl, benzyl or a group of the formula $R_2$CO— or $R_2SO_2$—, and $R_2$ represents $C_1$-$C_4$-alkyl, phenyl, or phenyl substituted by $C_1$-$C_4$-alkyl, halogen or $C_1$-$C_4$-alkoxy, or R represents an alkenylene or alkynylene group each having 2-8 C atoms, or a radical of the formula —Ar—, —Ar—X—Ar—, —Ar—$(CH_2)_m$—, —$(CH_2)_m$—O—Ar—O—$(CH_2)_m$—, —$(CH_2)_m$—NH—Ar—NH—$(CH_2)_m$—, —$(CH_2)_m$—Ar—X—Ar—$(CH_2)_m$—, —$(CH_2)_m$—O—Ar—X—Ar—O—$(CH_2)_m$— or —$(CH_2)_m$—NH—Ar—X—Ar—NH—$(CH_2)_m$—, wherein m represents 1 or 2, and Ar represents a phenylene or naphthylene group which can be substituted by halogen, $NO_2$, alkyl or alkoxy each having 1-4 C atoms, and X represents a direct bond, —O—, —S—, —$SO_2$—, —$CH_2$—, —$C(CH_3)_2$— or —CO—, or R represents a bivalent heterocyclic radical of the formula —$(CH_2)_n$—Het—$(CH_2)_n$—, wherein n represents 0, 1 or 2, and Het represents a 5- or 6-membered non-condensed or condensed hetero ring having 1 to 3 N, O or S atoms, or a radical of the formula

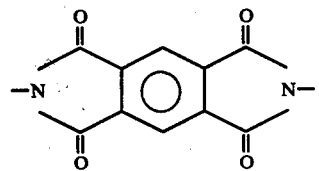

Preferred among these compounds are those wherein $R_1$ represents $C_1$-$C_4$-alkyl, phenyl, naphthyl, or phenyl substituted by $C_1$-$C_4$-alkyl or halogen, and R represents a direct bond, an alkylene group having 1-8 C atoms, or a radical of the formula —Ar— or —Ar—X—Ar, wherein Ar represents phenylene, and X represents a direct bond or —O—.

New compounds are on the other hand the compounds of the formula IV wherein R represents a $C_1$-$C_{10}$-alkylene group substituted by phenyl, benzyl, halogen, nitro, hydroxyl, $C_1$-$C_4$-alkoxy, formyl, $C_2$-$C_5$-alkanoyl, benzoyl or cyclohexylcarbonyl, or a $C_2$-$C_8$-alkylene group interrupted by —NY—, wherein Y represents hydrogen, $C_1$-$C_4$-alkyl, phenyl, naphthyl, cyclohexyl, benzyl, or a group of the formula $R_2$CO— or $R_2SO_2$—, and $R_2$ represents $C_1$-$C_4$-alkyl, phenyl, or phenyl substituted by $C_1$-$C_4$-alkyl, halogen, or $C_1$-$C_4$-alkoxy, or R represents a radical of of the formula —Ar—$(CH_2)_m$—, —$(CH_2)_m$—Ar—$(CH_2)_m$—, —$(CH_2)_m$—O—Ar—O—$(CH_2)_m$—, —$(CH_2)_m$—NH—Ar—NH—$(CH_2)_m$—, —$(CH_2)_m$—Ar—X—Ar—$(CH_2)_m$—, —$(CH_2)_m$—O—Ar—X—Ar—O—$(CH_2)_m$— or —$(CH_2)_m$—NH—Ar—X—Ar—NH—$(CH_2)_m$—, wherein m represents 1 or 2, and Ar represents a phenylene or naphthylene group which can be substituted by halogen, $NO_2$, $C_1$-$C_4$-alkyl or $C_1$-$C_4$-alkoxy, and X represents a direct bond, —O—, —S—, —$SO_2$—, —$CH_2$—, —$C(CH_3)_2$— or —CO—, or R represents a bivalent heterocyclic radical of the formula —$(CH_2)_n$—Het—$(CH_2)_n$—, wherein n represents 0, 1 or 2, and Het represents a 5- or 6-membered, non-condensed or condensed hetero ring having 1 to 3 N, O or S atoms, or a radical of the formula

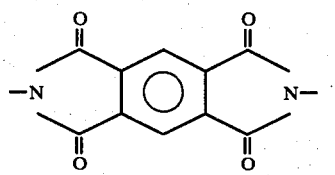

Preferred compounds among these are those wherein R represents a $C_1$-$C_8$-alkylene group substituted by phenyl, benzyl, hydroxyl, formyl, $C_2$-$C_5$-alkanoyl or benzoyl, or a $C_2$-$C_6$-alkylene group interrupted by —NY—, wherein Y represents phenyl or a group phenyl-$SO_2$—, or R represents a radical of the formula —$CH_2$—Ar—$CH_2$— or —$CH_2$—Ar—X—Ar—$CH_2$—, wherein Ar represents phenylene and X represents a direct bond or —O—.

The new compounds defined herein are likewise part of the present invention.

Thermoplastic materials (thermoplasts) which can be foamed according to the invention are, for example, polyolefins such as polyethylene or polypropylene, polystyrene and styrene copolymers such as IPS or ABS polymers, polyvinyl chloride, polyacetals, polycarbonates, aromatic polyethers, polysulphones and polysulphone ethers, polyesters such as polyethylene- or polybutyleneterepthalate, polyether esters, polyamides such as polycaprolactam, and also mixtures of such polymers. Since the decomposition temperature of the bis-tetrazoles of the formula I, II or III can be varied within certain limits by the choice of the bridge member R, plastics having different processing temperatures can be foamed.

In this manner, the bis-tetrazoles of the formula I, II or III are suitable for foaming at temperatures of 200° to above 300° C., preferably at 230° to 300° C. The process according to the invention is therefore suitable for the foaming of polypropylene, styrene copolymers, polycarbonates, aromatic polyethers and polyether sulphones, polyesters and polyamides.

The addition of the blowing agents to the plastics can be made by dry mixing, with preferably an adhesive being added. The adhesives used can be, for example, long-chain fatty acids or salts thereof, esters or amides. The blowing agents can also be added in the dissolved form, or in the form of a masterbatch. What generally applies is that the more uniformly the blowing agent is mixed with the plastics material, the more finely porous and homogeneous the foam becomes.

The foaming of the mixture of thermoplast and foaming agent is effected by known processes comprising heating with simultaneous moulding. The most important methods are injection moulding and extrusion. In the case of these two methods, the plasticised plastics material remains for only a relatively short space of time in the zone of the maximum processing temperature. Within this time all residues of the blowing agent which are still not decomposed should become decomposed. 5-Phenyltetrazole decomposes relatively slowly and, with uniform heating up, within a wide temperature range. The result is that the foamed plastics material still contains residues of the blowing agent, a condition which can lead to discoloration. This is not the case with the bis-tetrazoles used according to the invention, since these decompose within a relatively narrow temperature range. As is shown in the following Examples, no discoloration occurs with these blowing agents, irrespective of the plastics material used.

The amount of blowing agent added depends in the first place on the degree of foaming required; it depends also on the respective gas yield from the employed blowing agent. In general, 0.05 to 5% by weight of blowing agent, preferably 0.1 to 2% by weight, is used.

The thermoplasts used can contain additives such as are customary in plastics technology, such as fillers and reinforcing agents, glass fibres, pigments, lubricants, stabilisers, antistatic agents, nucleation agents, flameproofing agents, plasticisers, emulsifiers or optical brighteners. Such additives can be added simultaneously with the blowing agents.

The following Examples illustrate the production and use of the bis-tetrazoles of the formula I, II or III. Except where otherwise stated, 'parts' are parts by weight, the temperatures are given in degrees Centigrade, and percentages are percent by weight.

EXAMPLE 1

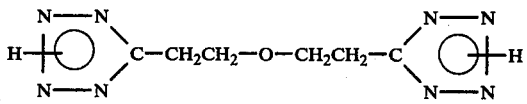

62 parts of di-(2-cyanoethyl)-ether are stirred together with 71.5 parts of sodium azide, 58.8 parts of ammonium chloride and 200 parts of dimethylformamide for 8 hours at 130°. After the addition of 30 parts of 30% hydrochloric acid, the reaction mixture is concentrated by evaporation to dryness, and extracted with 300 parts of absolute alcohol. The alcohol solution is concentrated to 100 parts by evaporation and cooled; there crystallises on cooling 1,5-bis-(5-tetrazolyl)-3-oxapentane which, after being filtered off and dried, melts at 192°–194°.

EXAMPLE 2

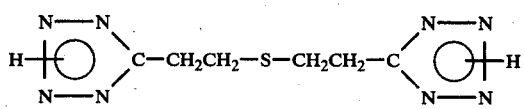

70.1 parts of thiodipropionitrile are stirred with 71.5 parts of sodium azide, 64.7 parts of ammonium chloride and 200 parts of dimethylformamide for 8 hours at 120°–130°, with a gentle stream of nitrogen being simultaneously passed through. The dimethylformamide is expelled in vacuo; to the residue are then added 200 parts of 2N sodium hydroxide solution, and extraction is performed with ether. The aqueous phase is freed from the dissolved ether by heating, clarified with 10 parts of active charcoal and filtered, and 30 parts of 20% hydrochloric acid are added. The product, initially precipitated in oily form, crystallises on standing overnight. Recrystallisation from water yields crystals of 1,5-bis-(5-tetrazolyl)-3-thiapentane, which melt at 140°.

EXAMPLE 3

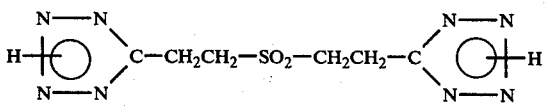

22.6 g of the compound of Example 2 is introduced into 400 parts of 10% potassium bicarbonate solution. At 70° are added dropwise 600 parts of a 5% potassium permanganate solution. The precipitated $MnO_2$ is dissolved with sodium bisulphite, and the pH value is adjusted to 2 with concentrated hydrochloric acid. The precipitated di-(β-5-tetrazolyl-ethyl)-sulphone is recrystallised from water, and melts at 252°.

EXAMPLE 4

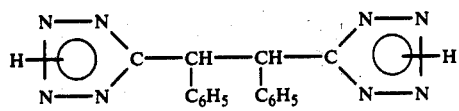

23 parts of 2,3-diphenylsuccinic acid dinitrile, 18.2 parts of sodium azide, 15 parts of ammonium chloride and 100 parts of dimethylformamide are stirred at 130°–140° for 15 hours. The mixture is poured into 1000 parts of water and crude 1,2-bis-(5-tetrazolyl)-1,2-diphenylethane precipitates out; this is then recrystallised from dimethylformamide/water and melts at 286°.

EXAMPLE 5

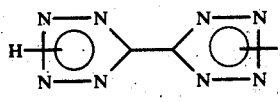

30 parts of ditetrazole sodium salt, produced according to data given in Example 2 of U.S. Pat. No. 2,710,297, are refluxed with 100 parts of water and 80 parts of concentrated hydrochloric acid for one hour. Concentration of the clear solution by evaporation yields crystals which melt at 263° after recrystallisation from water.

EXAMPLE 6

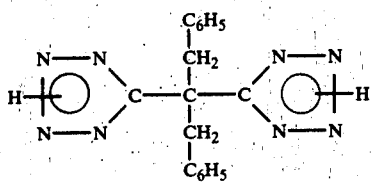

49.2 parts of dibenzyl malodinitrile are stirred with 31.2 parts of sodium azide, 25.7 parts of ammonium chloride and 200 parts of dimethylformamide, whilst a gentle stream of nitrogen is passed through, for 12 hours at 130°. After the dimethylformamide has been distilled off in vacuo, 500 parts of water are added to th residue, and the crude bis-tetrazole is dissolved by addition of 50% sodium hydroxide solution to give pH 10 at 40°. The solution is treated with animal charcoal, filtered and acidified. The crude product, precipitated in resinous form, is recrystallised from isopropanol/water 2:1 to obtain 1,3-diphenyl-2,2-di-(5-tetrazolyl)-propane, which melts at 228°–230°.

EXAMPLES 7 TO 23

The following bis-tetrazoles are produced by the process described in Example 1

| Compound Number | R | Melting point |
|---|---|---|
| 7 | $-CH_2-$ | 212° |
| 8 | $-(CH_2)_2-$ | 244° |
| 9 | $-(CH_2)_3-$ | 193° |
| 10 | $-(CH_2)_4-$ | 200° |
| 11 | $-(CH_2)_5-$ | 142° |
| 12 | $-(CH_2)_2-CH(CH_3)-$ | 157° |
| 13 | $-CH_2-O-CH_2-$ | 182° |
| 14 | $-(CH_2)_2-O-(CH_2)_2-O-(CH_2)_2-$ | 112° |
| 15 | $-CH_2-CH(OH)-CH_2-$ | 200° |
| 16 | $-CH_2-C_6H_4-C_6H_4-CH_2-$ | 295° |
| 17 | $-CH_2-C_6H_4-O-C_6H_4-CH_2-$ | 208° |
| 18 | $-C_6H_4-CH_2-$ | 280° |
| 19 | o-$C_6H_4(CH_3)(CH_2-)$ | 235° |
| 20 | $-CH_2-C_6H_4-CH_2-$ | 260° |
| 21 | o-$C_6H_4(CH_2-)_2$ | 256° |
| 22 | $-CH_2CH_2-N(C_6H_5)-CH_2CH_2-$ | 230° |
| 23 | $-CH_2CH_2-N(SO_2C_6H_5)-CH_2CH_2-$ | 147° |

EXAMPLES 24 TO 27

The following bis-tetrazoles of the formula

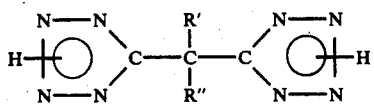

are produced by the process described in Example 6:

| Compound No. | | Melting point |
|---|---|---|
| 24 | R' = benzyl, R'' = H | 260° |
| 25 | R' = R'' = butyl | 144° |
| 26 | R' = R'' = propyl | 200° |

-continued

| Compound No. | | Melting point |
|---|---|---|
| 27 | R' = R" = ethyl | 202° |

EXAMPLE 28

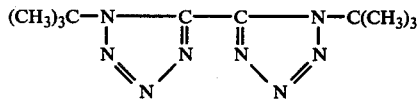

21.0 g of N,N'-di-tert.-butyloxalamide and 42.0 g of phosphorus pentachloride are slowly heated in 200 ml of benzene to 50°. The amide goes into solution with an intense evolution of HCl. As soon as the HCl evolution has ended, the reaction mixture is concentrated in vacuo to dryness. The residue is dissolved with cooling in 100 ml of dimethylformamide. This solution is added dropwise to a suspension of 17 g of sodium azide in 50 ml of dimethylformamide. The reaction mixture is heated for 3 hours at 100°, and then poured into 500 ml of water. The crystals obtained are separated and recrystallised from ethanol to yield 1,1'-di-tert.-butyl-5,5'-bis-tetrazole having a melting point of 154°–155°.

EXAMPLES 29 TO 32

The following bis-tetrazoles of the formula

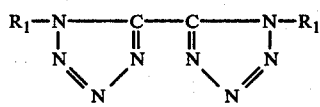

are produced by the process described in Example 28:

| Compound No. | $R_1$ | Melting point |
|---|---|---|
| 29 | ethyl | 82–83° |
| 30 | p-chlorophenyl | 257° |
| 31 | methyl | 201–202° |
| 32 | phenyl | 210–212° |

EXAMPLE 33

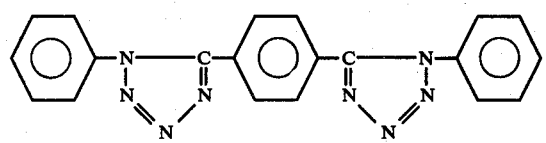

15.8 g of terephthalic acid dianilide and 20.8 g of $PCl_5$ are intimately mixed and the mixture is heated at a bath temperature of 180° for 2 hours. The formed $POCl_3$ is thereupon distilled off, and the residue is recrystallised from chlorobenzene. The imide chloride thus obtained crystallises in the form of small light-yellow flakes and melts at 195°–196°.

14.0 g of the imide chloride is refluxed with 5.8 g of $NaN_3$ in 100 ml of dimethylformamide for 2 hours. The reaction mixture is thereupon diluted with 400 ml of $H_2O$; the precipitated crystals are filtered off, washed with water and recrystallised from dimethylformamide. The resulting p-phenylene-5,5'-bis-(1-phenyltetrazole) melts at 295°–298°.

EXAMPLES 34 AND 35

The following bis-tetrazoles are produced by the process of Example 33:

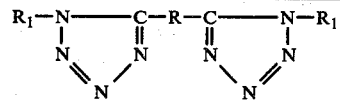

| Compound No. | R | $R_1$ | Melting point |
|---|---|---|---|
| 34 | p-phenylene | methyl | 258–260° |
| 35 | m-phenylene | phenyl | 203–205° |

EXAMPLE 36

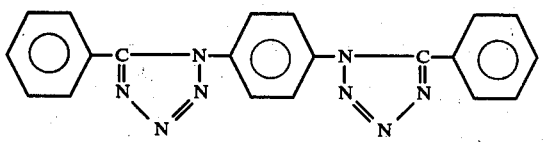

31.7 g of N,N'-dibenzoyl-p-phenylenediamine and 42.0 g of phosphorus pentachloride are intimately mixed and slowly heated. At 100°–120° there occurs an intense evolution of HCl. The reaction mixture is held at 150°–160° until the evolution of HCl has ceased, and is then concentrated by evaporation to dryness. The resulting crystalline imide chloride (melting point 195°–198°) is dissolved in 250 ml of dimethylformamide. Into this solution is introduced 13.0 g of sodium azide, and the reaction mixture is stirred for 3 hours at 140°–150° C. After cooling, it is diluted with 500 ml of water; the crystalline precipitate obtained is separated, and recrystallised from dimethylformamide. The resulting bis-tetrazole of the above formula melts at 274°.

EXAMPLE 37 m-Phenylene-1,1'-bis-(5-phenyltetrazole), which melts at 274°, is produced from N,N'-dibenzoyl-m-phenylenediamine by the process described in Example 36.

EXAMPLE 38

A commercial granulated polycarbonate which contains 5% of glass fibres (Lexan FL 900, General Electric) and which has a viscosity number of 0.495 and a density of 1.2 g/ccm, is dried for 2.5 hours in an oven at 120°. It is then preliminarily mixed for 20 minutes with 0.1% butyl stearate in order to ensure the adhesion of the blowing agent; it is subsequently mixed by tumbling with 0.3% by weight of 1,4-bis-(5-tetrazolyl)-butane (compound No. 10), and mixing is continued for a further 20 minutes in a Rhönrad mixer.

The mixture is processed in an injection moulding machine to give rectangular plates of 80 × 50 × 6 mm. The cylinder temperatures are 260°, 270° and 290° with a nozzle temperature of 280°. The cooling time in the mould is 50 seconds. The moulded shape obtained has a viscosity number of 0.485 and a density of 0.85 g/cm³. It has a smooth surface and a foamed core having a fine uniform pore structure and displays no discoloration.

A comparative test under the same conditions but with the use of 5-phenyltetrazole as the blowing agent produces a foamed specimen which has a pink-red discoloration. This discoloration becomed more severe with increase of the concentration of blowing agent.

EXAMPLE 39

A commercial polyphenylene oxide granulate (Noryl FN 215, AKZO) having a density of 1.06 g/cm³ is dried for 3 hours at 100° in vacuo. It is then mixed, as described in Example 38, with 0.1% of butyl stearate and 0.3% of 1,5-bis-(5-tetrazolyl)-3-oxapentane (compound No. 1). The mixture is processed as described in Example 38 in an injection moulding machine into the form of plates. The density of the foamed plates is 0.85 g/cm³.

EXAMPLE 40

A commercial granulated polybutyleneterephthalate (Crastin SK 605, Ciba-Geigy AG) having a glass-fibre content of 30% by weight and a density of 1.53 g/cm³ is dried for 8 hours at 100° in vacuo, and then mixed with 0.1% of butyl stearate and 0.3% of p-xylene-bis-(5-tetrazole) (compound No. 20). The mixture is processed, as described in Example 38, into plates, but the temperatures of the individual heating zones of the injection moulding machine are 250°, 270° and 270°, and 260° at the nozzle. The plates obtained have a density of 0.8 g/cm³.

A repeat of this test using however 5-phenyltetrazole as the blowing agent yields shaped specimens having a pink-red discoloration.

EXAMPLE 41

Comparative determination of the gas yield of various tetrazoles. By means of thermogravimetrical analysis there is determined the temperature of the maximum rate of decomposition with a temperature increase of 5°/minute for each individual tetrazole. At this temperature (rounded up or down to the nearest 10° of temperature) is determined the gas yield using the following procedure:

100-200 mg of substance is mixed in a small flask with ground stopper, having a content of about 8 ml, with 5 g of dry quartz sand. The flask is connected through a capillary tube to a 50 ml gas-burette. Paraffin oil is used as the sealing liquid. The small flask containing the specimen is brought, in a preheated bomb furnace, to the test temperature, and is held at this temperature until no further noticeable increase in volume occurs. For the purpose of correction, there is determined the blank volume which is formed by the thermal expansion of the air in the reaction flask. For this purpose, the reaction flask containing nothing but 5 g of quartz sand is brought, in an analogous manner, to the corresponding test temperature. The difference in the two measurements gives the volume of gas formed during decomposition. It is calculated in ml/g of substance.

The gas yields of various tetrazoles, determined in this manner, are shown in Table 1.

Table 1

Gas yield of bis-tetrazoles of the formula

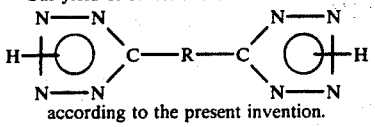

according to the present invention.

| R= | Measured temperature | Measured time in minutes | Gas volume ml/g |
|---|---|---|---|
| —(CH₂)₂— | 250° | 30 | 245 |
| —(CH₂)₄— | 270° | 20 | 242 |
| —(CH₂)₅— | 260° | 25 | 221 |
| —CH₂CH₂OCH₂CH₂— | 260° | 25 | 229 |
| —CH₂CH₂SCH₂CH₂— | 260° | 20 | 264 |
| (o-xylylene —CH₂-C₆H₄-CH₂—) | 260° | 25 | 190 |
| (p-xylylene —CH₂-C₆H₄-CH₂—) | 260° | 30 | 182 |
| direct bond | 250° | 30 | 245 |
| —CH₂CH₂SO₂CH₂CH₂— | 240° | 30 | 240 |
| —CH₂CH₂OCH₂CH₂OCH₂CH₂— | 260° | 20 | 189 |
| —CH(CH₂C₆H₅)— | 260° | 20 | 215 |

Comparison of monotetrazoles of the formula:

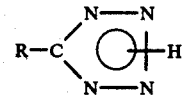

| R= | Measured temperature | Measured time in minutes | Gas volume ml/g |
|---|---|---|---|
| phenyl | 260° | 30 | 170 |
| phenyl | 300° | 30 | 180 |
| p-chlorophenyl | 250° | 25 | 135 |
| phthalimido | 290° | 25 | 73 |

EXAMPLE 42

A commercial polycarbonate granulate (Lexan FL 900, General Electric) is ground in a mill to a particle size of 315 μm. The polycarbonate contains 5% of glass fibres and has a density of 1.2 g/cm³. The polymer before processing is dried in an air-circulation furnace at 120° for 4 hours, and subsequently 50 g of the dried polycarbonate powder is homogeneously mixed with 0.3 g of each of the following bis-tetrazoles:
(a) 1,2-bis-(5-tetrazolyl)-ethane (compound No. 8), and
(b) 1,5-bis-(5-tetrazolyl)-3-oxapentane (compound No. 1).

In each case 6 g of the mixture is placed into a cylindrical aluminium mould, lockable by screwing and having a capacity of 11 cm³, and the closed mould is transferred to a furnace at 340°. After a holding time of 12 minutes - the foamed plastics material attains in this time a maximum temperature of 320° — the mould is removed from the furnace and cooled with cold water. The specimens removed from the mould have a density of 0.47–0.50 g/cm³, a smooth surface, and a foamed core having a fine and homogeneous pore structure. Compared with a comparative specimen without a blowing agent, the foamed specimens exhibit no change of coloration.

EXAMPLE 43

A commercial polyphenylene oxide granulate (Noryl FN 215, General Electric) is ground in a mill to obtain a particle size of 400 μm. It has a density of 1.06 g/cm³ and before being processed it is dried for 3 hours at 100° in an air-circulation furnace; and subsequently 50 g of the polyphenylene oxide powder is homogeneously mixed with 0.3 g of each of the following bis-tetrazoles:
(a) α,p-bis-(5-tetrazolyl)-toluene (compound No. 18),
(b) 1,3-diphenyl-2,2-di-(5-tetrazolyl)-propane (compound No. 6),
(c) 4,4'-bis-(5-tetrazolylmethyl)-diphenyl (compound No. 16),
(d) 1,1-bis-(5-tetrazolyl)-2-phenylethane (compound No. 24),
(e) di-(β-5-tetrazolyl-ethyl)-sulphone (compound No. 3),
(f) 1,1'-diphenyl-5,5'-bis-tetrazole (compound No. 32),
(g) α,α'-bis-(5-tetrazolyl)-p-xylene (compound No. 20),
(h) 1,5-bis-(5-tetrazolyl)-3-oxapentane (compound No. 11)
(i) 1,5-bis-(5-tetrazolyl)-3-oxapentane (compound No. 1),
(k) 1,2-bis-(5-tetrazolyl)-ethane (compound No. 8),
(l) N,N-bis-[2-(5-tetrazolyl)-ethyl]-aniline (compound No. 22),
(m) 1,4-bis-(5-tetrazolyl)-butane (compound No. 10).

In the manner described in Example 42, 7.5 g in each case of the mixture in a mould of 11 cm³ capacity is foamed by being heated for 12 minutes in a furnace at 340° (maximum internal temperature = 230°). The foamed specimens have a density of 0.58–0.71 g/cm³, a smooth surface, and a foamed core having a fine and homogeneous pore structure. The tetrazoles used cause no change of colour.

EXAMPLE 44

A commercial polybutyleneterephthalate (Crastin S 600, Ciba-Geigy AG) is ground in a mill to obtain a particle size of 400 μm. It has a density of 1.31 g/cm³ and before processing it is dried for 6 hours at 100° in a vacuum drying cabinet. In each case 50 g of the PBT powder is homogeneously mixed with 0.3 g of each of the following bis-tetrazoles:
(a) 1,5-bis-(5-tetrazolyl)-3-oxapentane (compound No. 1), and
(b) 1,5-bis-(5-tetrazolyl)-3-thiapentane (compound No. 2).

As described in Example 42, 6 g of each of these mixtures is heated in a closed mould for 12 minutes in a furnace at 340° (max. internal temperature = 310°). The moulded specimens have a density of 0.48–0.50 g/cm³, a smooth surface, and a foamed core having a fine and homogeneous pore structure. The tetrazoles used cause no change of colour.

EXAMPLE 45

A commercial polyamide 6 (Grilon A 28, Emser-Werke AG) is ground in a mill to obtain a particle size of 400 μm. The material has a density of 1.14 g/cm³, and before processing it is dried for 6 hours at 80° in a vacuum drying cabinet. Then 50 g in each case of the polyamide powder is homogeneously mixed with 0.3 g of each of the following bis-triazoles:
(a) 1,5-bis-(5-tetrazolyl)-pentane (compound No. 11),
(b) 1,5-bis-(5-tetrazolyl)-3-oxapentane (compound No. 1),
(c) 1,2-bis-(5-tetrazolyl)-ethane (compound No. 8), and
(d) 1,4-bis-(5-tetrazolyl)-butane (compound No. 10).

In the manner described in Example 42, 6.5 g of each of these mixtures is heated in a closed mould for 12 minutes in a furnace at 340° (max. internal temperature = 290°). The moulded specimens obtained have a density of 0.51–0.54 g/cm³, a smooth surface, and a foamed core having a fine and homogeneous pore structure. The tetrazoles used cause no change of colour.

EXAMPLE 46

50 g of a commercial polypropylene powder (Proprathene HF 20, Imperial Chemical Industries), having a density of 0.9 g/cm³ and a particle size of 250 μm, is mixed in each case with 0.3 g of 1,5-bis-(5-tetrazolyl)-3-oxapentane (compound No. 1) and 0.05 g of a commercial antioxidant (Irganox 1010, Ciba-Geigy AG) to obtain a homogeneous mixture. As described in Example 42, 5 g of this mixture is foamed in a closed mould by the mould being heated for 12 minutes in a furnace at 375° (max. internal temperature = 330°). The specimens on removal have a density of 0.45 g/cm³, a smooth surface, and a foamed core having a fine and homogeneous pore structure. The tetrazoles used cause no change of colour.

EXAMPLE 47

A commercial low-pressure polyethylene (Vestolen A 6016, Chemische Werke Hüls AG) having a density of 0.962 g/cm³ is ground in a mill to give a particle size of 315 μm. 50 g of the polyethylene powder is homogeneously mixed with 0.3 g of 1,3-bis-(1-phenyl-5-tetrazolyl)-benzene (compound No. 35), and, as described in Example 42, 5 g in each case of this mixture is heated in a closed mould for 12 minutes in a furnace at 375° (max. internal temperature = 290°). The specimens obtained have a density of 0.41 g/cm³, a smooth surface, and a foamed core having a fine and homogeneous pore structure. The tetrazoles used cause no change of colour.

EXAMPLE 48

50 g of an impact-resistant polystyrene powder (Experimental product of the firm Belgochim) having a particle size of 400 μm and a density of 1.05 g/cm³ is homogeneously mixed with 0.05 g of a commercial antioxidant (Irganox 1076, Ciba-Geigy AG) and 0.3 g of N,N-bis-[2-(5-tetrazolyl)-ethyl]-benzenesulphoneamide (compound No. 23). In the manner described in Example 42, 5.1 g of the mixture is foamed by heating the mould for 15 minutes in a furnace at 280° (max. internal temperature = 258°). The specimen obtained has a density of 0.42 g/cm³, a smooth surface, and a foamed core having a fine and homogeneous pore structure. The tetrazoles used cause no change of colour.

I claim:
1. Process for foaming a thermoplastic resin, which process comprises adding to the thermoplast 0.05 to 5% by weight of a bis-tetrazole of the formula I, II or III

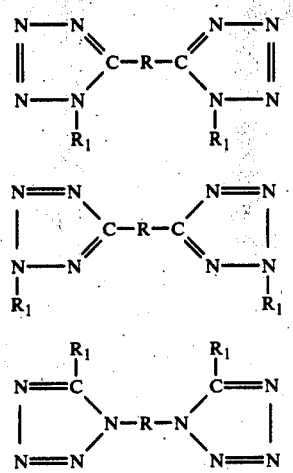

wherein R₁ represents hydrogen, $C_1$–$C_4$-alkyl, $C_5$–$C_6$-cycloalkyl, phenyl, naphthyl, or phenyl substituted by $C_1$–$C_4$-alkyl, $C_1$–$C_4$-alkoxy or halogen, and R represents a direct bond, or a straight-chain or branched-chain alkylene group having 1–10 C atoms, which can be substituted by phenyl, benzyl, halogen, nitro, hydroxy, $C_1$–$C_4$-alkoxy, formyl, $C_2$–$C_5$-alkanoyl, benzoyl or cyclohexylcarbonyl, or R represents an alkylene group which has 2–8 C atoms and which is interrupted by —O—, —S—, —SO₂— or —NY—, wherein Y represents hydrogen, $C_1$–$C_4$-alkyl, phenyl, naphthyl, cyclohexyl, benzyl, or a group of the formula $R_2CO$— or $R_2SO_2$—, and R₂ represents $C_1$–$C_4$-alkyl, phenyl, or phenyl substituted by $C_1$–$C_4$-alkyl, halogen or $C_1$–$C_4$-alkoxy, or R represents an alkenylene or alkynylene group each having 2–8 C atoms, or a radical of the formula —Ar—(CH₂)ₘ—, —(CH₂)ₘ—Ar—(CH₂)ₘ—, —(CH₂)ₘ—O—Ar—O—(CH₂)ₘ—, —(CH₂)ₘ—N-H—Ar—NH—(CH₂)ₘ—, —(CH₂)ₘ—Ar—X-—Ar—(CH₂)ₘ—, —(CH₂)ₘ—O—Ar—X-—Ar—O—(CH₂)ₘ—, or —(CH₂)ₘ—NH—Ar—X-—Ar—NH—(CH₂)ₘ—, wherein m represents 1 or 2, and Ar represents a phenylene or naphthylene group, which can be substituted by halogen, NO₂, alkyl or alkoxy each having 1–4 C atoms, and X represents a direct bond, —O—, —S—, —SO₂—, —CH₂—, —C(CH₃)₂ or —CO—, or R represents a bivalent heterocyclic radical of the formula —(CH₂)ₙ—Het—(CH₂)ₙ—, wherein n represents 0, 1 or 2, and Het represents a 5- or 6-membered, non-condensed or condensed hetero ring having 1 to 3 N, O or S atoms, or a radical of the formula

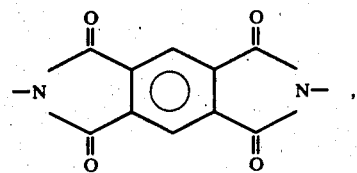

or R represents in the formula III a group of the formula —Ar— or —Ar—X—Ar— or, if R₁ is not hydrogen, represents also in the formula I or II a group of the formula —Ar— or —Ar—X—Ar—; and subsequently heating the mixture.

2. Process according to claim 1, wherein the thermoplastic resin is selected from the group consisting of polypropylene, a styrene copolymer, a polycarbonate, an aromatic polyether or polysulphone ether, a polyester or a polyamide; and foaming is performed at 230°–300° C.

3. Process according to claim 1, in which there is used a bis-tetrazole of the formula I wherein R₁ represents hydrogen $C_1$–$C_4$-alkyl, phenyl, or phenyl substituted by $C_1$–$C_4$-alkyl or by chlorine, and R represents a direct bond, an alkylene group which has 1–10 C atoms and which can be substituted by phenyl, benzyl, hydroxyl, formyl, $C_2$–$C_5$-alkanoyl or benzoyl, or a $C_2$–$C_8$-alkylene group interrupted by —O—, —S—, —SO₂— or —NY—, wherein Y represents $C_1$–$C_4$-alkyl, phenyl, benzyl, $R_2CO$— or $R_2SO_2$—, and R₂ represents $C_1$—$C_4$-alkyl, phenyl or tolyl, or R represents $C_2$–$C_8$-alkenylene, $C_2$–$C_8$-alkynylene or a radical of the formula —(CH₂)ₘ—Ar—(CH₂)ₘ— or —(CH₂)ₘ—Ar—X-—Ar—(CH₂)ₘ—, wherein m represents 1 or 2, Ar represents phenylene or naphthylene which can be substituted by $C_1$–$C_4$-alkyl, $C_1$–$C_4$-alkoxy, halogen or NO₂, and X represents a direct bond, —O—, —S—, —SO₂—, —CH₂— or —CO—, or, if R₁ is not hydrogen, R represents $C_6$–$C_{12}$-arylene or —Ar—X—Ar—.

4. Process according to claim 1, in which there is used a bis-tetrazole of the formula I wherein R₁ represents hydrogen, and R represents a direct bond or a straight-chain or branched-chain alkylene group which has 1–10 C atoms and which can be substituted by 1 or 2 phenyl or benzyl groups, an alkylene group which has 2–8 C atoms and which is interrupted by —O—, —S—, —SO₂— or —NY—, wherein Y represents alkyl having 1–4 C atoms, phenyl or benzyl, an alkenylene or alkynylene group each having 2–8 C atoms, or a radical of the formula —(CH₂)ₘ—Ar—(CH₂)ₘ or —(CH₂)ₘ—Ar—X—Ar—(CH₂)ₘ—, wherein m represents 1 or 2, and Ar represents a phenylene or naphthylene group which can be substituted by halogen, NO₂, alkyl or alkoxy each having 1–4 C atoms, and X represents a direct bond, —O—, —S—, —SO₂—, —CH₂— or —CO—.

5. Process according to claim 1, in which there is used a bis-tetrazole of the formula I wherein R₁ represents hydrogen, $C_1$–$C_4$-alkyl or phenyl, and R represents a direct bond, an alkylene group which has 1–8 C atoms and which can be substituted by 1 or 2 phenyl or benzyl groups, an alkylene group which has 2–6 C atoms and which is interrupted by —O—, —S—, —SO₂— or —NY—, wherein Y represents phenyl, benzoyl, benzenesulphonyl or toluenesulphonyl, or a radical of the formula —CH₂—Ar—CH₂— or —CH₂—Ar—X-—Ar—CH₂—, wherein Ar represents phenylene, and X represents a direct bond or —O—.

6. A process according to claim 3 wherein R₁, in the bistetrazole of formula I, is hydrogen.

* * * * *